United States Patent [19]

Leuck et al.

[11] Patent Number: 4,554,392

[45] Date of Patent: Nov. 19, 1985

[54] METHOD OF PREPARING 1,2-DICHLOROETHANE FROM ETHYLENE AND CHLORINE GAS

[75] Inventors: Hans Leuck; Hans-Jörg Westermann, both of Troisdorf, Fed. Rep. of Germany

[73] Assignee: Dynamit Nobel AG, Troisdorf, Fed. Rep. of Germany

[21] Appl. No.: 668,649

[22] Filed: Nov. 6, 1984

[30] Foreign Application Priority Data

Nov. 10, 1983 [DE] Fed. Rep. of Germany ....... 3340624

[51] Int. Cl.$^4$ ............................................. C07C 17/02
[52] U.S. Cl. ..................................... 570/254; 570/253
[58] Field of Search ........................ 570/254, 253, 252

[56] References Cited

U.S. PATENT DOCUMENTS 4,347,391 8/1982 Campbell ............................ 570/254

Primary Examiner—Charles F. Warren
Assistant Examiner—Joseph A. Boska
Attorney, Agent, or Firm—Felfe & Lynch

[57] ABSTRACT

In this method of producing 1,2-dichloroethane from ethylene and chlorine gas in an approximately equimolar ratio at reaction pressures between 2 and 20 bar, at ethylene dichloride boiling temperatures between 105° and 225° C., in the presence of catalysts acting as Lewis acids, the catalyst-free ethylene dichloride vapors produced in the evaporative cooling are withdrawn and then condensed and cooled, and liquid catalyst-containing ethylene dichloride is also withdrawn separately.

All of the gaseous chlorine input, having a purity of about 90 to 100% by volume, is introduced into a condensed and cooled circulating stream of ethylene dichloride. The ethylene dichloride stream containing chlorine is brought to the reaction pressure, and then catalyst-containing ethylene dichloride withdrawn from the reactor is admixed.

The ethylene dichloride stream, containing chlorine and catalyst, is heated while the catalyst-free ethylene dichloride stream is cooled, and from the latter the end product ethylene dichloride is taken as a partial stream. An ethylene partial stream is fed into the downward stream of the reactor. The downward stream, upon contact with a main input of ethylene introduced at the bottom of the reactor at a mass rate between 30 and 200 kg/sec·m$^2$ is reversed into an upward stream forming a highly disperse gas-liquid phase.

7 Claims, 1 Drawing Figure

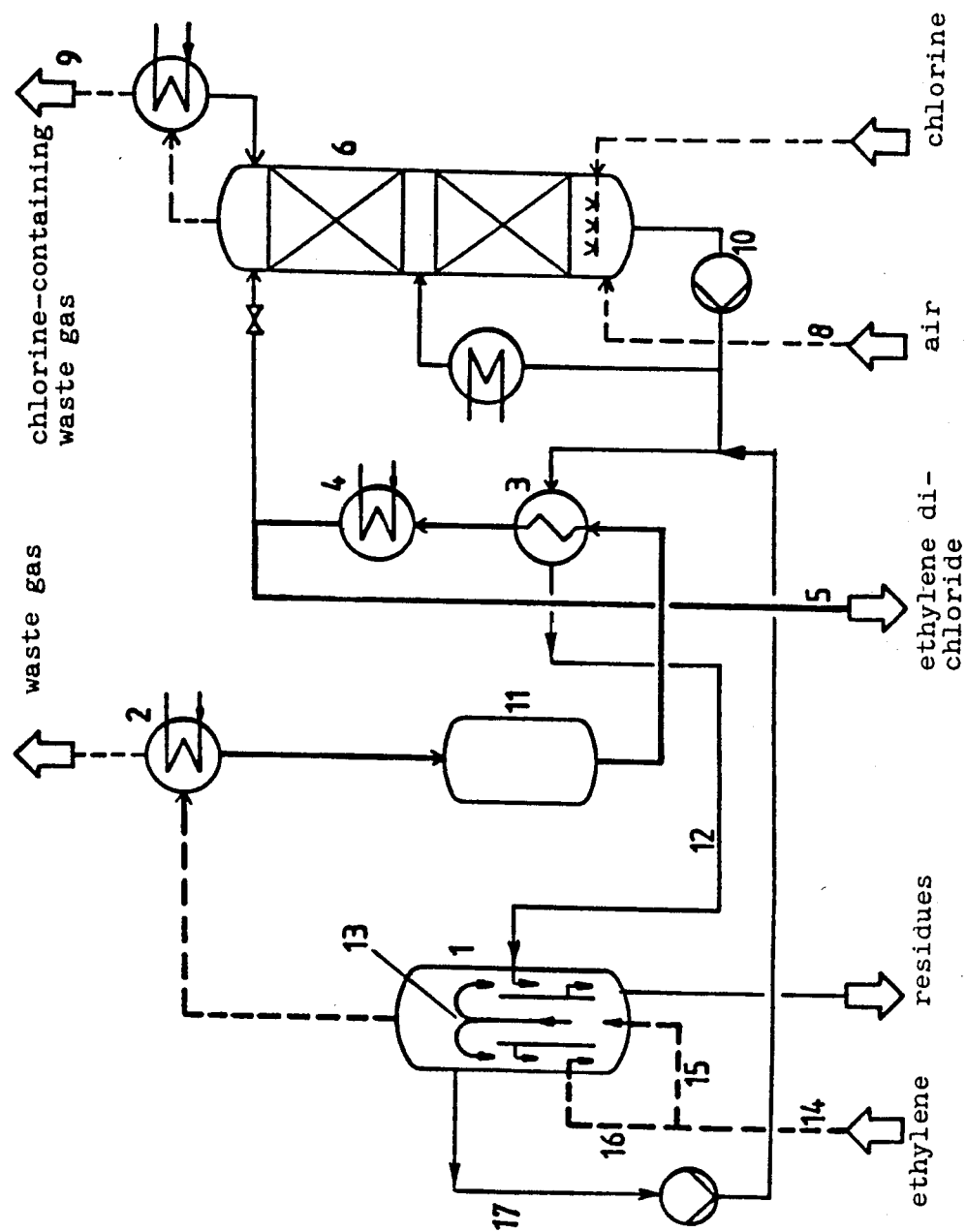

METHOD OF PREPARING 1,2-DICHLOROETHANE FROM ETHYLENE AND CHLORINE GAS

BACKGROUND OF THE INVENTION

The present invention is in a method for preparing 1,2-dichloroethane from ethylene and chlorine gas.

It is known to prepare 1,2-dichloroethane (hereinafter alos referred to as ethylene dichloride) by reacting ethylene with chlorine in liquid ethylene dichloride in the presence of Lewis acid catalysts. The known large-scale processes operate continuously, at standard pressure or slightly elevated pressure, below or at the boiling temperature of ethylene dichloride. The object in this case is to achieve high volume-time yields and product yields along with a very complete conversion of the ethylene, and, by removing the considerable heat of reaction, maintaining a constant temperature in the reactor (cf. German Pat. No. 2,427,045). To accomplish this object, different approaches are used.

For example, the reaction heat is removed by a cooling system installed within the reactor, or the performance of the chlorination reaction on the one hand and the removal of the reaction heat on the other are carried out in separate apparatus, heat being removed from the product by temperature reduction in coolers disposed outside of the reactor. The effectiveness of either cooling system is gradually impaired by incrustation with complex compounds and poorly soluble products, so that difficult cleaning operations are required at intervals of time to sustain the performance of the apparatus.

German Offenlegungsschrift No. 29 35 885 describes a combination of expedient chemical and process engineering measures by which, among other things, the main reaction of the addition of chlorine onto ethylene is performed at pressures of 0.3 to 1.3 bar and temperatures of 50° to 90° C., and at least half of the chlorine is used in solution in the cooled reaction product and the rest of the chlorine is added in gaseous and/or liquid form.

More recent methods operate at temperatures of over 100° C. in order to have a sufficient temperature level for utilization of the reaction heat of about one ton of steam per ton of ethylene dichloride. The heat removal is performed again by direct cooling of the reactor contents or by the evaporative cooling of ethylene dichloride, the regeneration of the reaction heat being performed as a rule by cooling or condensing with condensate with steam recovery, or other units of the process are heated directly with the vapors of ethylene dichloride that are produced.

Other differences lie in the feeding of the ethylene and chlorine starting products into the reaction system and in the use of atmospheric oxygen as a process adjuvant. In a number of methods the reaction gases are introduced directly into the reactor, and in others they are entirely or partially brought in contact with ethylene dichloride in mixers and dissolvers situated outside of the reactor, and then brought to the reaction.

In such techniques, the preparation of ethylene dichloride at elevated temperature and hence elevated pressure creates special problems due to the cell chlorine derived from a chlorine-alkali electrolysis and the gaseous impurities contained therein, of up to 10% (hydrogen, nitrogen, oxygen and carbon dioxide gases). Thus the chlorine gas must be compressed to a pressure between 5 and 20 bar, depending on the reaction temperature, and this is difficult and requires a great deal of energy.

Furthermore, the exhaust gases leaving the reaction system after the separation of the ethylene dichloride contain small amounts of hydrogen chloride and chlorine, which are usually neutralized with soda lye. The resultant mixture of residual soda lye, sodium chloride, sodium hypochlorite and sodium carbonates in water, has to be disposed of. The same need exists in the withdrawal of liquid ethylene dichloride from the reactor and the then necessary neutralization of the hydrogen chloride; in addition to the above-mentioned waste substances, a considerable amount of iron hydroxide sludge is produced if iron(III) chloride is used as catalyst in the decanting apparatus for separating the organic and aqueous phases. When the necessary periodical cleaning work is performed, and during the rest of the process, substance losses occur, and the catalyst losses must be constantly made up.

It is an object of the invention to avoid any chlorine gas compression and largely supress the formation of higher chlorinated products and chlorine containing distillation residues.

BRIEF DESCRIPTION OF THE DRAWING

The FIGURE is a flow diagram schematically illustrating the method of the invention.

THE INVENTION

Referring to the drawing, vapors consisting essentially of ethylene dichloride and produced from the reaction of the mixture (subsequently described) in reactor 1 are condensed in condenser 2 for steam generation, and, with the interposition of a receiver 11, are cooled in additional heat exchangers 3 and 4 down to 30° to 40° C. From the product stream leaving exchanger 4 an amount of raw ethylene dichloride product is withdrawn through pipeline 5 for further processing to the end product. The remainder corresponds approximately to 5 to 8 times the amount taken by pipeline 5 and is used as absorbent for dissolving the input chlorine in absorber 6. Accordingly, the stream 7 leaving the absorber has a chlorine concentration between about 8 and 13% by weight. At a reactor temperature of 105° C., the chlorine forepressure in accordance with the solubility of chlorine in ethylene dichloride, is to be at least 2.5 bar, while at a reactor temperature of 225° C. the chlorine forepressure needs to amount to only about 1.2 bar. At the same time, the gaseous components carbon dioxide and oxygen contained in the chlorine—if cell chlorine obtained from chlorine-alkali elextrolysis is used—are completely dissolved, but hardly any hydrogen and nitrogen.

The extensive absorption of the carbon dioxide increases the overall economy of the process because a chlorine-containing exhaust gas free of carbon dioxide, stream 9, is delivered from the absorber, after extensive removal of ethylene dichloride, to a system for neutralization with aqueous soda lye. The resultant solution can be used as a bleaching bath.

It is known generally that elemental oxygen has a positive effect on the selectivity of the reaction of the addition of elemental chlorine onto ethylene. Therefore, a preferred embodiment of the method according to the invention consists in introducing the oxygen additionally, in the form of air—stream 8—into the chlorine absorption system, instead of directly into the reactor as usual. The introduction of oxygen hinders the formation of undesired products, such as 1,1,2-trichloroethane.

After the chlorine absorption has been performed at low pressure, the solution of chlorine and ethylene dichloride thus obtained is pressurized by pump 10 to the desired elevated reactor pressure. This pressurized stream is added to stream 17 which contains the ethylene dichloride and catalyst withdrawn from the reactor. This combined stream flows countercurrently to the condensed vapors in heat exchanger 3. In exchanger 3, the solution temperature is raised to 20° C. or less lower than the reaction temperature. This heating is necessary to evaporate a sufficient amount of ethylene dichloride in the reactor 1, and so that after vapor condensation in condenser 2 enough ethylene dichloride will be present in the receiver 11 to dissolve the input chlorine in absorber 6. This temperature elevation causes a portion of the absorbed chlorine, depending on the solution equilibrium, to evaporate, causing a two-phase stream to form in the heat exchanger 3. It has been found that the selectivity of the reaction is adversely affected if gas phase reactions between chlorine and ethylene can occur, resulting in undesirable byproducts, especially higher chlorinated byproducts. It is important, in the method of the invention, that this evaporated chlorine be back in solution before it is brought together with the input ethylene. This is achieved by using the loop-reactor principle in reactor 1, by which a large, circulating, chlorine-free, catalyst-containing current 13 of ethylene dichloride is superimposed on the chlorine-containing two-phase input stream 12.

The quantity ratio of the two streams 12 and 13 is selected such that the chlorine concentration in the total stream, taking into account the reaction temperature and the lowering of the chlorine partial pressure by evaporating ethylene dichloride, is no more than corresponds to the solubility concentration of chlorine in ethylene chloride.

It is furthermore generally known that both the conversion and the selectivity of the ethylene dichloride formation is also affected by the catalyst concentration. Studies have shown that the conversion increases, up to a certain catalyst concentration, and then remains approximately constant. Surprisingly, however, it has been found that the selectivity decreases at higher catalyst concentrations, and with it the substance yield. In an advantageous embodiment of the process according to this invention, the catalyst concentration, in the case of the iron(III) chloride catalyst used, is between 300 and 1000 weight-parts per million.

The invention offers the special advantage that the required catalyst concentration in the chief reaction zone can be precisely controlled by the ethylene side stream 16, by the magnitude of the ethylene dichloride circulation and by the amount of the recycled stream 17 carrying catalyst.

The manner in which the ethylene is combined with the circulating ethylene dichloride containing chlorine and catalyst is characteristic of the present method. Studies (Balasubramanian, S.N. et al, IGC Fund, 5 (1966) 184) and assignee's experiments have shown that the reaction between ethylene and chlorine takes place instantaneously, and that the equilibrium is heavily on the side of 1,2-dichloroethane. This reaction is virtually complete, the mass transfer being the speed-determining factor. In the present method, therefore, care is taken to see that, by means of the gaseous reactant ethylene—stream 14—hydrodynamic conditions are made to prevail in its contact with the liquid phase, in the heterogeneous gas-liquid system which then is present in reactor 1, which promote the transfer of substance between the phases. This can be brought about by introducing most of the ethylene used as the substance stream 14 in the form of substance stream 15 through one or more nozzles into the reactor 1 at mass rates between 30 and 200 kg per sq m per second [kg/m$^2$·sec], such that, upon contact with the chlorine-containing and catalyst-containing downward stream, the latter is turned into the upward stream. This brings about a highly disperse state in the reacting gas-liquid mixture, and the other part of the input ethylene is used as a substance stream 16 in the annular chamber of the reactor to control the rate of circulation of the liquid.

The following Examples 1 to 3 are given for the further description of the present invention:

EXAMPLE 1

In a jacketed reactor of steel material, approximately 4 liters of high-purity ethylene dichloride (hereinafter EDC) are placed with 1000 weight-ppm of iron(III) chloride, and heated to the reaction temperature.

In an especially designed nozzle, such as a two-substance ring-gap mixing nozzle, first catalyst-free EDC is mixed with catalyst-containing EDC and high-purity chlorine before this solution is brought to reaction with ethylene, which is injected at a mass rate of approximately 35 kg/m$^2$·sec.

The vapors that form in the reaction are condensed and returned to the bottom part of the reactor, after withdrawal of the amount of product that has formed.

Due to the mixing effect of the nozzle, catalyst concentrations are produced in the bottom part of the reactor of approximately 50 to 70% of the average concentration of 1,000 ppm. 0.61 kg/h of ethylene and 1.6 kg/h of chlorine gas are used, corresponding to a chlorine excess of about 3.5%. The reaction temperature was 135° C. After a period of 5 h, the gas feed was shut off and the reactor content was rapidly cooled through the jacket.

Evaluation gave the following results:
Ethylene conversion: 99.9%, of which 90.2% was converted to EDC;
this is a yield of 90.1% of the theory.

EXAMPLE 2

The procedure and temperature were as in example 1, but the average catalyst concentration was reduced to 200 ppm.
Result:
Ethylene conversion: 96.1%; of which 90% was converted to EDC;
this is a yield of about 86.5% of the theory.

EXAMPLE 3 (Given for comparison)

In a 2-liter reactor of carbon steel with cooling jacket, stirrer, gas introduction and removal system, and a pressure measuring system, 0.8 liter of EDC was placed, together with 1000 ppm of iron(III) chloride, and stirred thoroughly at 120° C. Ethylene and chlorine were introduced in equimolar amounts into the bottom part of the reactor, until a system pressure of about 10 bar establishes itself, which is created by undissolved gases. After about 15 minutes, the reaction of the ethylene re-established the pressure related to 120° C. This procedure was repeated about 20 times. Due to the way the experiment was conducted, the conversion was virtually 100%. The yield was about 57% (average of several experiments).

It will be understood that the specification and examples are illustrative but not limitative of the present invention and that other embodiments within the spirit and scope of the invention will suggest themselves to those skilled in the art.

We claim:

1. A process for the preparation of 1,2-dichloroethane from ethylene and chlorine gas in an approximately equimolar ratio, at reaction pressures between 2 and 20 bar and boiling temperatures of the formed ethylene dichloride between 105° and 225° C. in the presence of catalysts acting as Lewis acids, containing the steps of removing catalyst-free vapors consisting essentially of ethylene dichloride and catalyst-containing liquid ethylene dichloride from a reactor and condensing and cooling the vapors to form a condensed and cooled stream of ethylene dichloride; comprising:

introducing gaseous chlorine, which has a purity of about 90 to 100 vol.-%, into the condensed and cooled stream of ethylene dichloride to absorb chlorine therein;

pressurizing the chlorine-containing ethylene dichloride stream to reaction pressure and then admixing the catalyst-containing ethylene dichloride;

heating the chlorine-containing and catalyst-containing ethylene dichloride stream;

feeding into a downward stream of the reactor an ethylene partial stream; and contacting the downward stream with a main ethylene input quantity introduced at the bottom of the reactor at a mass rate between 30 and 200 kg/sec·m$^2$ of this ethylene quantity whereby said downward stream is reversed into an upward stream forming a highly disperse gas-liquid phase.

2. The process of claim 1 wherein the heating of the chlorine-containing and catalyst-containing ethylene dichloride stream is by cooling of the catalyst free ethylene dichloride stream from which end product is removed as a partial stream.

3. The process of claim 1 wherein atmospheric oxygen is additionally introduced into the chlorine absorption stage.

4. The process of claim wherein all of the gaseous chlorine used is introduced into the condensed and cooled circulating stream of ethylene dichloride at a chlorine forepressure of about 1.2 to at least 2.5 bar.

5. The process of claim 1 wherein the chlorine-containing and catalyst-containing ethylene dichloride stream is heated up to a temperature that is 20° C. or less below the reaction temperature.

6. The process of claim 1 wherein the rate of circulation is controlled in the reactor by the feeding of an ethylene partial stream into the downward stream of the reactor.

7. The process of claim 1 wherein, in the upward stream of the reactor, a catalyst concentration of 300 to 1000 wt.-ppm is maintained.

* * * * *

UNITED STATES PATENT AND TRADEMARK OFFICE
CERTIFICATE OF CORRECTION

PATENT NO. : 4,554,392

DATED : November 19, 1985

INVENTOR(S) : Hans Leuck et al

It is certified that error appears in the above-identified patent and that said Letters Patent is hereby corrected as shown below:

Column 1, line 10, "alos" should be --also--

Column 6, line 17, following the word "claim" insert --1--

Signed and Sealed this

Twelfth Day of August 1986

[SEAL]

Attest:

Attesting Officer

DONALD J. QUIGG

Commissioner of Patents and Trademarks